United States Patent [19]

Grimwood

[11] Patent Number: 5,119,032
[45] Date of Patent: Jun. 2, 1992

[54] DETECTION OF IMPERFECTIONS IN THE INERT COATING OF A ROTATING METAL COMPONENT

[75] Inventor: Geoffrey L. Grimwood, Huddersfield, England

[73] Assignee: Thomas Broadbent & Sons Limited, Huddersfield, United Kingdom

[21] Appl. No.: 572,165

[22] Filed: Aug. 23, 1990

[30] Foreign Application Priority Data

Aug. 25, 1989 [GB] United Kingdom ............... 8919324
Apr. 26, 1990 [GB] United Kingdom ............... 9009365

[51] Int. Cl.⁵ .............................................. G01B 31/12
[52] U.S. Cl. .................................................. 324/557
[58] Field of Search ....................... 324/557, 558, 559

[56] References Cited

U.S. PATENT DOCUMENTS 4,188,267 4/1980 Gaud et al.
4,240,878 12/1980 Carter
4,543,525 9/1985 Borytra et al. ................... 324/559
4,558,273 12/1985 Nishimara ......................... 324/558
4,584,521 2/1985 Gaud et al.

FOREIGN PATENT DOCUMENTS

WO8301514  4/1983  European Pat. Off.
1499632     2/1978  United Kingdom
1545487     5/1979  United Kingdom
2195771     4/1988  United Kingdom

OTHER PUBLICATIONS

Industrial Laboratory, vol. 53, No. 2, Feb., 1987.
Patent Abstracts of Japan, vol. 9, No. 109 (P380) (1922).

Primary Examiner—Walter E. Snow
Attorney, Agent, or Firm—Tilton, Fallon, Lungmus

[57] ABSTRACT

A method and apparatus for testing, in situ, for imperfections in an inert coating of a moving metal component of an apparatus (e.g. a metal basket of a centrifuge) involves covering the inert coating with an electrically conductive liquid, applying an electrical voltage across the inert coating while the apparatus is operational, monitoring the current or applied voltage, and utilizing the measured current or voltge to provide an indication of the condition of the inert coating. If the coating is defective, the conductive liquid will find its way into any flaws or imperfections, thereby providing a path of lower electrical resistance.

38 Claims, 6 Drawing Sheets

DETECTION OF IMPERFECTIONS IN THE INERT COATING OF A ROTATING METAL COMPONENT

The present invention relates to a method for detecting wear on metal assemblies having inert coatings thereon, and more particularly, though not exclusively, to a method of detecting wear on steel centrifuge baskets having inert coatings. The invention also relates to apparatus, e.g. centrifuges, adapted to enable said method to be applied.

The separation of solids from liquids or the separation of two liquids in chemical and mineral processes is often conducted by means of centrifugation. Many of the liquids subjected to centrifugation are electrically conducting and corroding liquids and at elevated temperature (40° C.), the normally non-corroding steels from which the centrifuge components can be made are prone to stress corrosion. For this reason the machinery used has metal components which have an inert coating or covering for protection against corrosion.

Carbon steel and other similar metals protected by an inert coating are in common use in centrifuge baskets where contact with corrosive electrically conducting liquids occur. These coated metal components are prone to catastrophic failure if the corroding liquid penetrates small cracks and pinholes in the coating. These small cracks and pinholes are not readily detectable. Thus, where the assembly is under mechanical stress it is necessary, for both safety and operational reasons, periodically to subject the assembly to tests in order to determine if any cracks, pinholes or other discontinuities have developed. This testing procedure is particularly important for rotating and highly stressed centrifuge baskets. Currently it is necessary to remove the baskets from the centrifuge to conduct these tests, and this seriously reduces the time the centrifuge is operational.

It is an object of the invention to provide a means for testing for imperfections in the inert coatings of moving metal components in situ and whilst operational, in order to reduce "down" time.

According to one aspect of the present invention there is provided a method for testing, in situ, for imperfections in an inert coating of a moving metal component of an apparatus, characterised by covering the coating with an electrically conductive liquid, applying an electrical voltage across the inert coating while the apparatus is operational, monitoring the resulting current or applied voltage, and utilising the monitored current or voltage to provide an indication of the condition of the inert coating.

In order to apply the method it is necessary to modify existing apparatus such as centrifugation machinery.

It is a further object of the invention to provide an apparatus e.g. a centrifuge, embodying one or more coated moving metal components e.g. baskets, and having two electrical contacts, a first contact on or connected to the inert coating of the or each moving metal component and a second contact on or connected to the metal of the component, which two contacts form part of an electrical circuit which will be completed if a discontinuity fault in the coating occurs to allow current to pass through the inert coating, means being provided for such a current to give an indication of the existence of the fault.

According to another aspect of the present invention there is provided an apparatus adapted to have an inert coating of a moving metal component tested for imperfections during operation, comprising means for covering the coating with an electrically conductive liquid, a first electrical contact on or in use contacting the inert coating of the moving component, a second electrical contact on or in use contacting the moving metal component, said electrical contacts being linked by conductive parts of the apparatus to form a complete circuit via the conductive liquid if the inert coating on the component is damaged, and means for detecting completion of such a circuit.

In one embodiment, the electrical contact with the inert coating is made via the liquid, since the inert coating must be wetted with a conductive liquid if its whole area is to be tested.

In one embodiment a first electrical contact member may be provided on a conductive feed indicator slipper or shoe, which is electrically insulated from the feed indicator, which member contacts the inert coating on the inside of the moving metal component in use via the liquid and a second contact member provided on the metallic moving part of the apparatus, which member contacts the metal of the basket itself.

During a cycle of operation the apparatus is part-filled with a conductive liquid. By suitably insulating either a stationary part of the apparatus (e.g. a feed indicator or a wash pipe jet) or the moving metal component, an electrical voltage may be applied between these stationary and moving parts of the apparatus and appears on the inside and outside of the inert coating. If the inert coating is not damaged (i.e. is in good condition), the "leakage" current flowing as a result of the applied voltage will be small. If, however, the inert coating is damaged and hence is discontinuous, a larger, "fault" current will flow between the contacts, and can be detected to indicate inert coating failure. Typically, the "fault" current will be more than ten times the "leakage" current.

The principle of the method will be clear from the preceding embodiment, and it will be appreciated that existing apparatus, e.g. a centrifuge, can be modified, to allow the method to be applied, in a variety of ways.

In another embodiment the contacts to the coating on the inside of the moving metal component may be provided via a wash pipe which is electrically insulated from the metal parts of the apparatus. The second contact member may again be provided on a moving metallic part of the apparatus, which part is indirectly attached to the metal of the coated component. In this embodiment, as in the previous embodiment, the liquid completes the circuit. This time, however, it is a jet of electrically conducting liquid from the nozzle of the wash pipe which makes electrical contact with the inert coating. The liquid contacts residual liquid on the inert coating so that the whole coating is tested.

The same method and apparatus can be used to test the inert coating on the outside of the component. This may be achieved by the same principle, but by providing an electrical connection on the outside of the component. Thus, an outer wash pipe may be electrically insulated and provided with an electrical contact. Again, by delivering a jet of an electrically conducting liquid to the outside of the component from the wash pipe, a circuit with a contact leading from the metal component to rotating parts of the apparatus on which the component is mounted, can be made.

The applied voltage may be alternating or unidirectional, and a test circuit may be provided on the apparatus to establish that the voltage is being applied. This test circuit may be connected to an audio or visual safety alarm circuit.

The embodiments outlined have a rubbing contact as one of the contact members, but other forms could be utilised. For example, in some situations, it may be preferred to have a stator instead of a rubbing contact to avoid wear between moving parts and the risk of sparking, or it may be preferred to apply a contact infrequently and only when testing the inert coating.

In an alternative embodiment one contact to the inert coating on the moving component is provided either by an uninsulated feed limiter or a jet of conducting liquid from an uninsulated wash pipe (i.e. both feed indicator and wash pipe are of conventional design and make metallic contact with the stationary parts of the apparatus). With the moving component insulated from the stationary parts of the apparatus the second contact to the inert coating is made to the insulated component through the spindle upon which the insulated component is mounted. This may be achieved by having a conductive rod movable within a cavity in the spindle (preferably a blind bore along the rotational axis), which is moved into electrical contact with the bottom of the cavity when it is desired to test the coating. Thus contact to conducting liquid inside the component by the feed limiter or wash jet allows a voltage to be applied to test the inert coating of the component.

Alternatively, the moving component may additionally be insulated from the spindle upon which it is mounted, and electrical contact to the component may be made by a conductive rod movable in an aperture (preferably a bore along the rotational axis) extending right through the spindle to the component. With the first contact being provided by an uninsulated feed limiter or a jet of conducting liquid from an uninsulated wash pipe, as before, the second contact is provided by moving the rod through the aperture in the spindle into electrical contact with the component. This arrangement is particularly useful if the apparatus is used in conditions where condensation might occur.

Several embodiments of the invention will now be described by way of example only, with reference to the accompanying drawings, in which:

FIG. 3 illustrates two alternative arrangements to the rubbing contact of FIG. 2;

Figure 1:
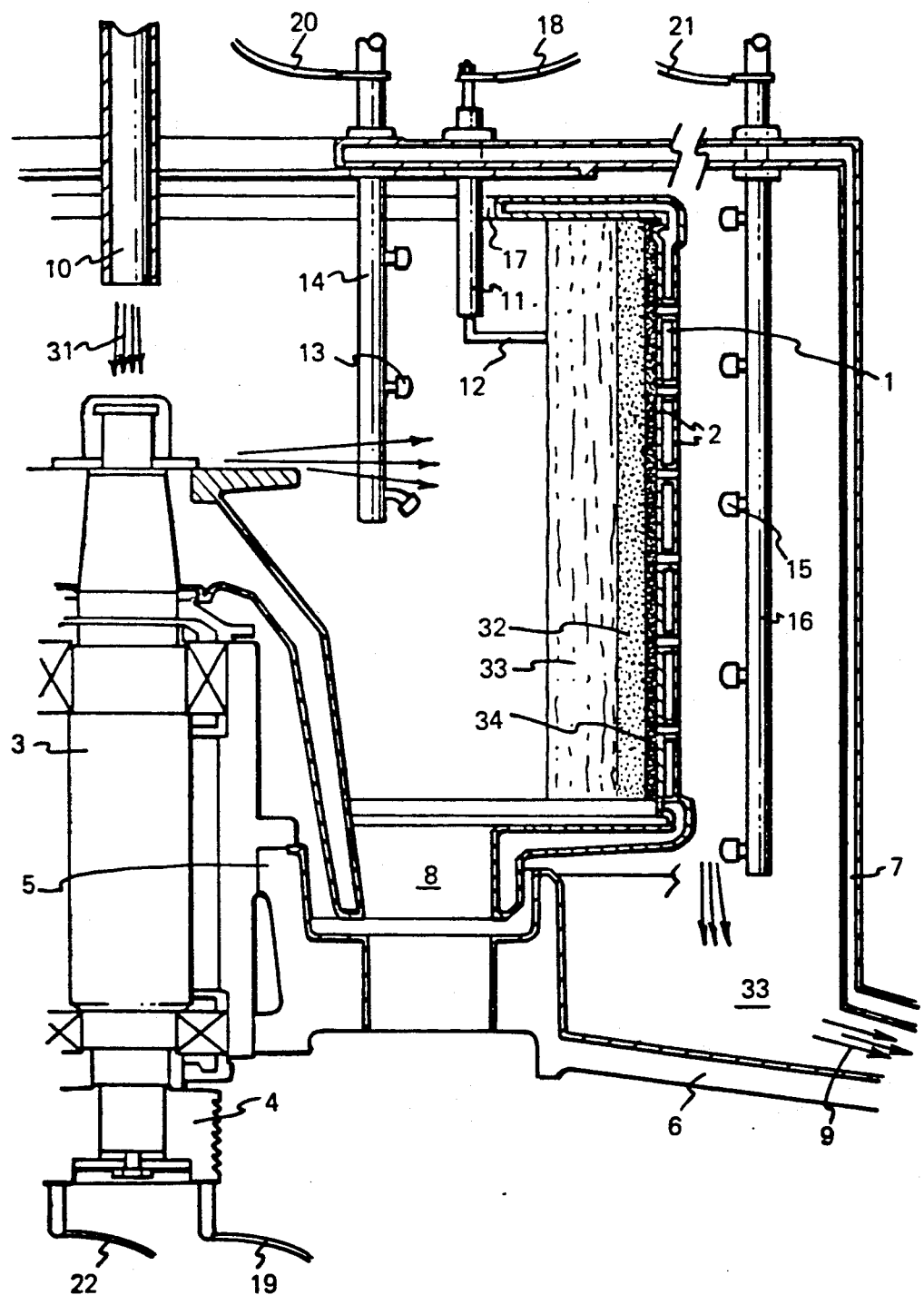
FIG. 1 illustrates in part section a first embodiment of centrifuge in accordance with the present invention, adapted, in three alternative modes, for testing the inert coating of an uninsulated centrifuge basket.

Referring to FIG. 1, a typical centrifuge comprises a perforated metal basket 1, protected by an inert coating 2 which is mounted on a vertical spindle 3 that rotates when driven by pulley 4 in the bearing housing 5 mounted in the stationary base 6. An outer casing 7 that surrounds the basket is also mounted onto the base 6. The basket 1 has at least one opening 8 through which the separated solids are discharged downwardly and the outer casing 7 has at least one opening through which the separated liquid 9 is discharged radially. Slurry 31 (a mixture of solids 32 and liquids 33) to be separated flows into the basket 1 through the slurry inlet pipe 10. A feed indicator 11 is provided enabling a feed indicator shoe 12 to rotate to touch the surface of liquid 33 or solids 32 spinning in the basket, thereby controlling the slurry feed and monitoring the amount of slurry in the basket. Provision is made to wash the separated solids in the basket and, if necessary, to clean the basket interior by having wash liquid flow from nozzles 13 in wash pipe 14 mounted inside the basket. Similarly the outside of the basket may be cleaned by having wash liquid flow from nozzles 15 in wash pipes 16 mounted between the basket 1 and the outer casing 7. A plough discharger, (not shown) is also fitted when the separated solids are discharged through opening 8 in the basket 1. Solids may also be discharged by means of a suction device (not shown) through the top opening of the basket.

A typical process cycle consists of slurry feed, from inlet pipe 10 entering the rotating basket, being accelerated and moved outwardly to the inner wall of the basket 1 by centrifugal force. The solids move to the wall of the basket to form a bed 34 through which the liquid permeates, passing through the perforations 2 in the basket 1 to the outer casing 7 to flow as separated liquid from the liquid outlet 9. The continuing slurry flow builds up the solids bed thickness at the basket wall. The feed indicator shoe 12 is positioned onto the surface of the liquid to control the slurry flow. In some applications with high liquid flow rates the separated liquid spills over a basket lip 17 during the initial stages of slurry flow. When sufficient slurry/solids have been supplied to the centrifuge the slurry flow is stopped and the basket continues to rotate to drain surplus liquid from the annular bed of solids. During or after this drain period the rotating solids in the basket may be washed by liquid supplied to wash pipe 14 at sufficient pressure for the liquid to flow from nozzles 13 to the inner surface of the solids bed and thence to the liquid outlet 9 via the perforations in the basket 1. When the separation and washing is complete the discharger removes the bulk of the solids from the inner basket wall. The cycle is then repeated continuously.

The discharge plough leaves a thin layer or "heel" of solids on the inner basket wall at the end of each cycle which accumulate with successive cycles. Periodically, after a series of cycles (typically ten), the bed is removed by washing using liquid flow from the wash pipe nozzles (13) to dissolve the heel.

To monitor the inert coating of the highly stressed components of the basket and assess any deterioration or discontinuity in the inert coating, the centrifuge may be constructed such that the conducting feed indicator slipper 12 is insulated electrically from the feed indicator 11 and provided with an electrical connection 18 and a rubbing electrical contact or brush 19 is made to the metallic rotating part of the centrifuge. At a convenient place in the centrifuge cycle when the basket is part full of liquid and the electrically insulated feed indicator slipper is in contact with the inner liquid surface in the basket (FIG. 2) an electrical voltage is applied to connections 18 and 19. The metallic parts of the centrifuge and the conducting liquid in the basket apply this voltage across the inert coating protecting the metal of the basket. As the inert coating is non-conducting and if it is in good condition, the current flowing as a result of the applied voltage will be finite but very small. If the inert coating is cracked, abraded, has pin holes or other discontinuities and the conducting corrosive liquid has penetrated to the basket metal, a substantial current will flow, indicating deterioration and the onset of corrosion.

In an alternative arrangement the wash pipe 14 is electrically isolated from the metal parts of the centrifuge and provided with an electrical connection 20, the pipework and tanks supplying the wash liquid being similarly insulated or made of non-conducting material. Again at a convenient place in the centrifuge cycle the voltage is applied to connections 19 and 20 when wash liquid from at least one nozzle 13 is flowing as a jet and not in droplets. This liquid jet makes electrical contact with the liquid in the basket, replacing the contact made by the conducting feed indicator slipper 12 and monitoring the inert coating of the metal basket can be carried out as previously.

The alternative arrangement described above may be extended to monitor the condition of the inert coating on the outside of the basket 1 by insulating the wash pipe 16 and its associated pipework and tanks and providing an electrical connection 21. The electrical voltage is applied to connections 19 and 21 when wash liquid from at least one nozzle 15 is flowing as a jet and the remaining nozzles 15 are delivering wash liquid to the outside of the basket—thus monitoring the inert coating as described above.

Figure 2:
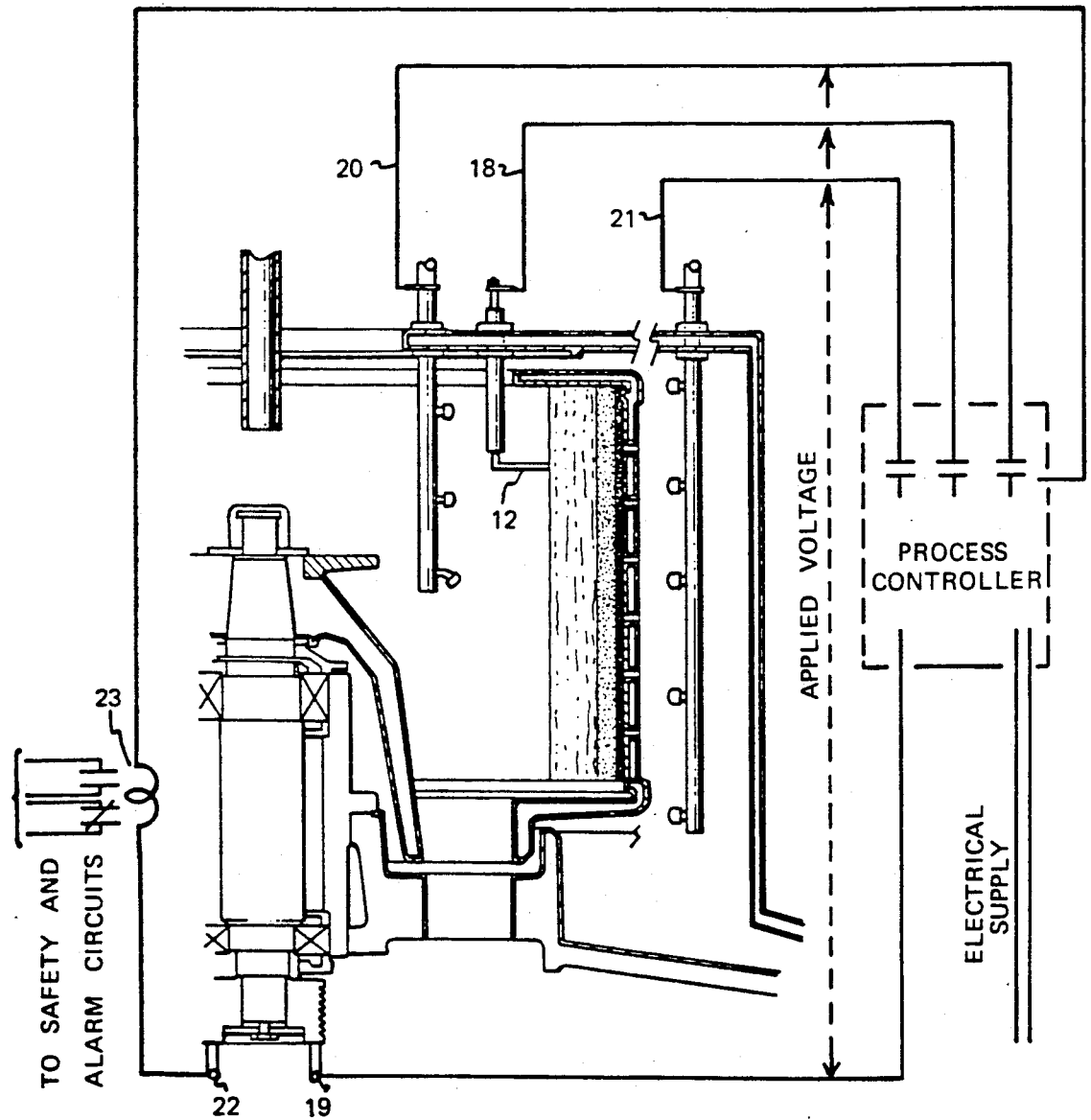
FIG. 2 illustrates the electrical arrangement of a centrifuge of the type illustrated in FIG. 1.

In one preferred electrical arrangement, for a centrifuge constructed as FIG. 1, as shown in FIG. 2, voltage is applied to an additional rubbing contact 22 which is made to the metallic rotating part of the centrifuge to ensure that the monitoring system voltage is present, a relay 23 or equivalent contacts being connected to the centrifuge safety circuits to give a warning signal upon voltage failure. The various contact pairs 18 and 19, 19 and 20, 19 and 21 are connected as shown in FIG. 2 to the centrifuge process controller which applies the voltage and monitors the inert coating in the appropriate part of the centrifuge cycle (or after a multiple number of cycles) when the required liquid distribution is present in the basket. The process controller will also signal the projection of the feed indicator shoe 12 (or a similar liquid contacting device if it is impractical to use the feed indicator shoe) if contact to the liquid surface is required.

An alternative electrical arrangement uses a unidirectional applied voltage, the polarity of which may be applied to reduce by cathodic protection the corrosive action resulting from the conducting liquid coming into contact with the metallic part of the basket—whilst providing the monitoring of the inert coating as described above.

Figure 3A:
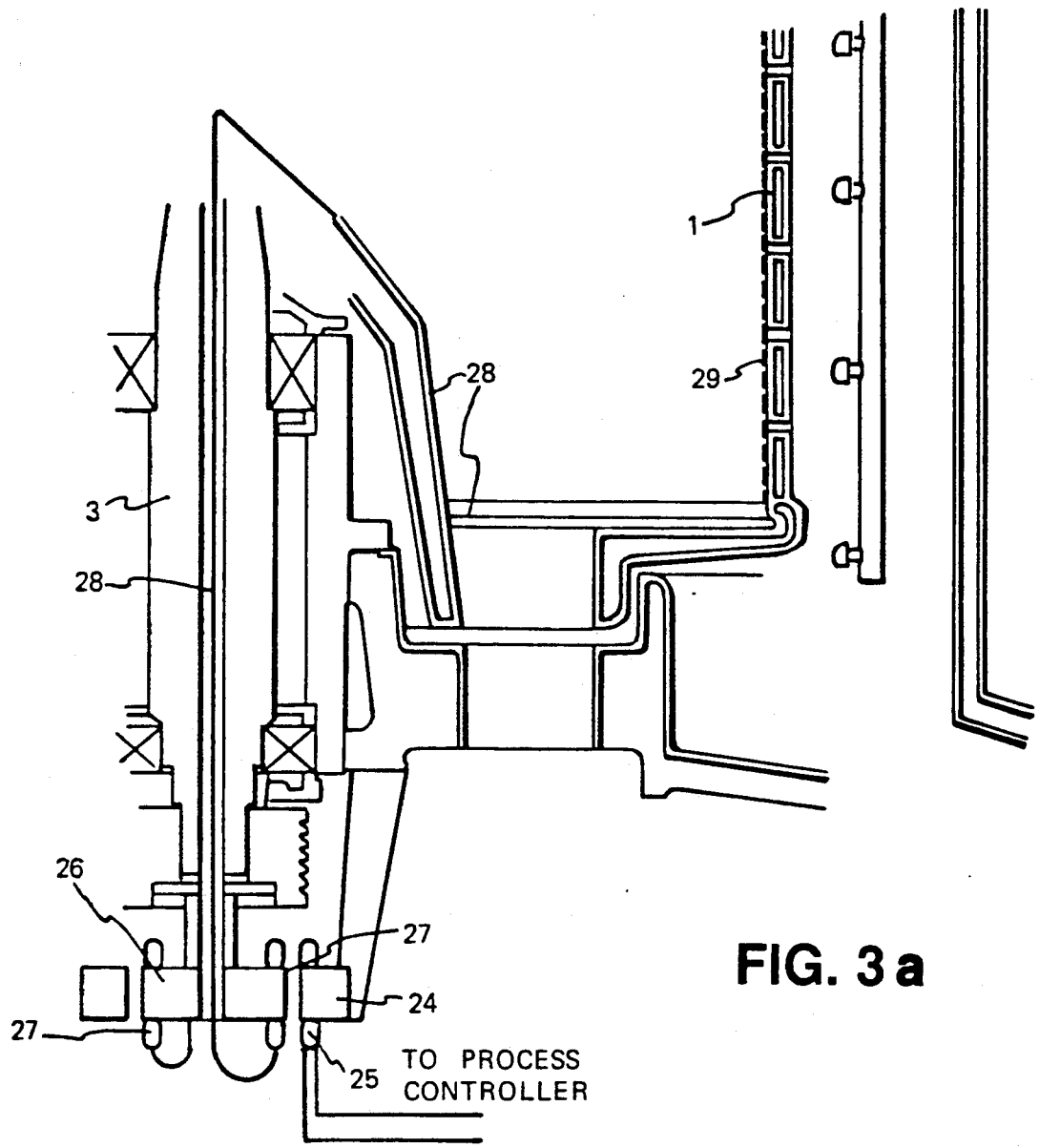
FIG. 3a is for an A.C. supply.
Figure 3B:
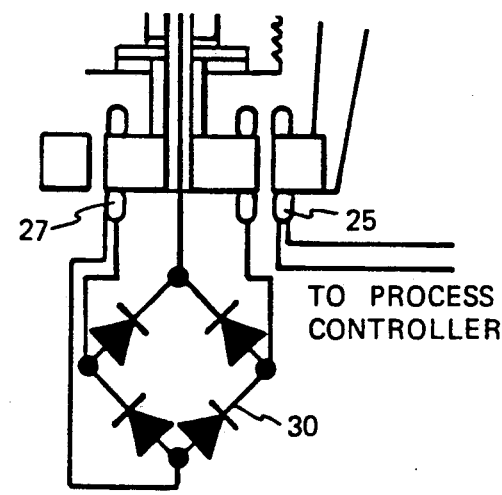
FIG. 3b is for a D.C. supply.

An alternative to the rubbing contact 19 may be fitted by inducing the voltage required for monitoring the inert coating. FIG. 3 shows a stator 24 of at least one winding 25 in an annulus of magnetic material which surrounds a rotor 26 fitted with at least one winding 27. One end of the winding 27 is connected to the rotating basket metal via the shaft 3 and the other by means of an insulated conductor 28 placed through the shaft and along the basket bottom to a conducting perforated screen or the equivalent 29 placed against or near the inert coating of the inner basket wall, thus applying the induced voltage across the inert coating. When a failure occurs in the inert coating increased current flows in the rotating winding 27 resulting in a corresponding increase in the current in the stationary winding 25. The connection of the stationary winding 25 to connections 18 and 19 (FIG. 2) in place of the rubbing contacts connects this arrangement to the process controller to monitor the inert coating of the basket.

By introducing rectifiers 30 in the connections from the rotating winding 27 this alternative arrangement applies a unidirectional voltage to the inert coating to continue cathodic protection with the monitoring of the inert coating as already described.

It should be noted that as an alternative to the direct electrical contact with the inert coating via the conductor 28, the conductor 28 may be dispensed with and replaced with electrical contact via the feed indicator slipper in contact with the liquid layer or via either wash pipe 14 or 16, as described for the previous embodiment. In that case, the only difference from the first embodiment would be the replacement of the rubbing contact.

Figure 4:
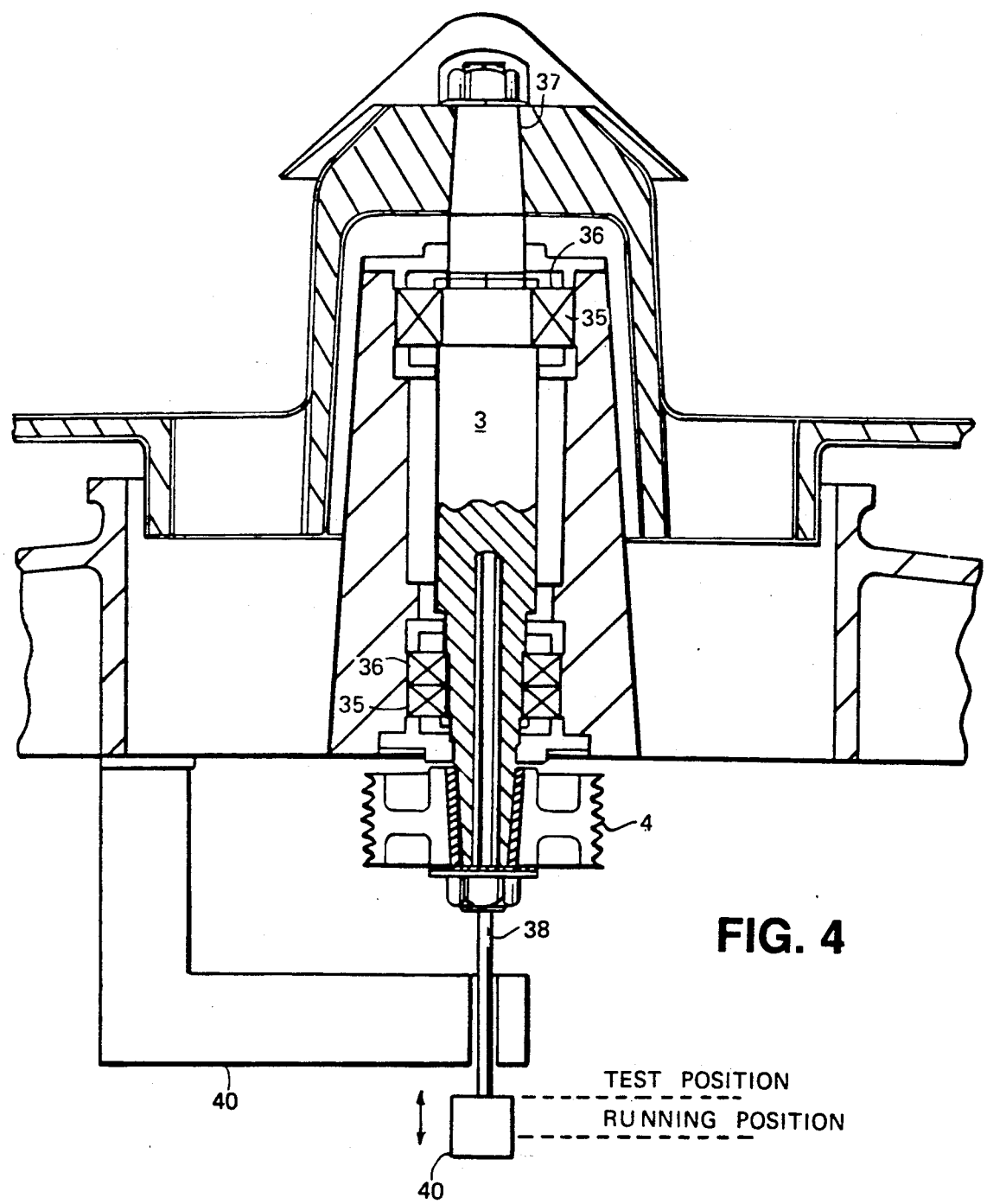
FIG. 4 is a cross-section through a spindle of a second embodiment of centrifuge in accordance with the present invention.

An alternative arrangement is shown in part section in FIG. 4. The arrangement is generally similar to that of FIGS. 1 and 2, and the same reference numerals are used for the same features. The differences occur on the centrifuge spindle 3 which is fitted with upper and lower bearings 35, the outer surfaces of which are coated with a hard insulating material (such as plasma sprayed aluminium oxide) 36 to insulate the spindle 3 from the bearing housing 5. The spindle 3 makes metallic contact with the centrifuge basket 1 at the mounting taper 37. The first electrical contact is made to the basket via the spindle and a rod 38 that passes through a clearance hole drilled on the spindle axis. The rod 38 is held on the axis of the spindle 3 by a sleeved bracket 40 and can be raised by mechanism 41 (typically a pneumatic cylinder) to make contact with the shaft only when testing the inert coating. The rod is electrically connected to the process controller as before.

Figure 5:
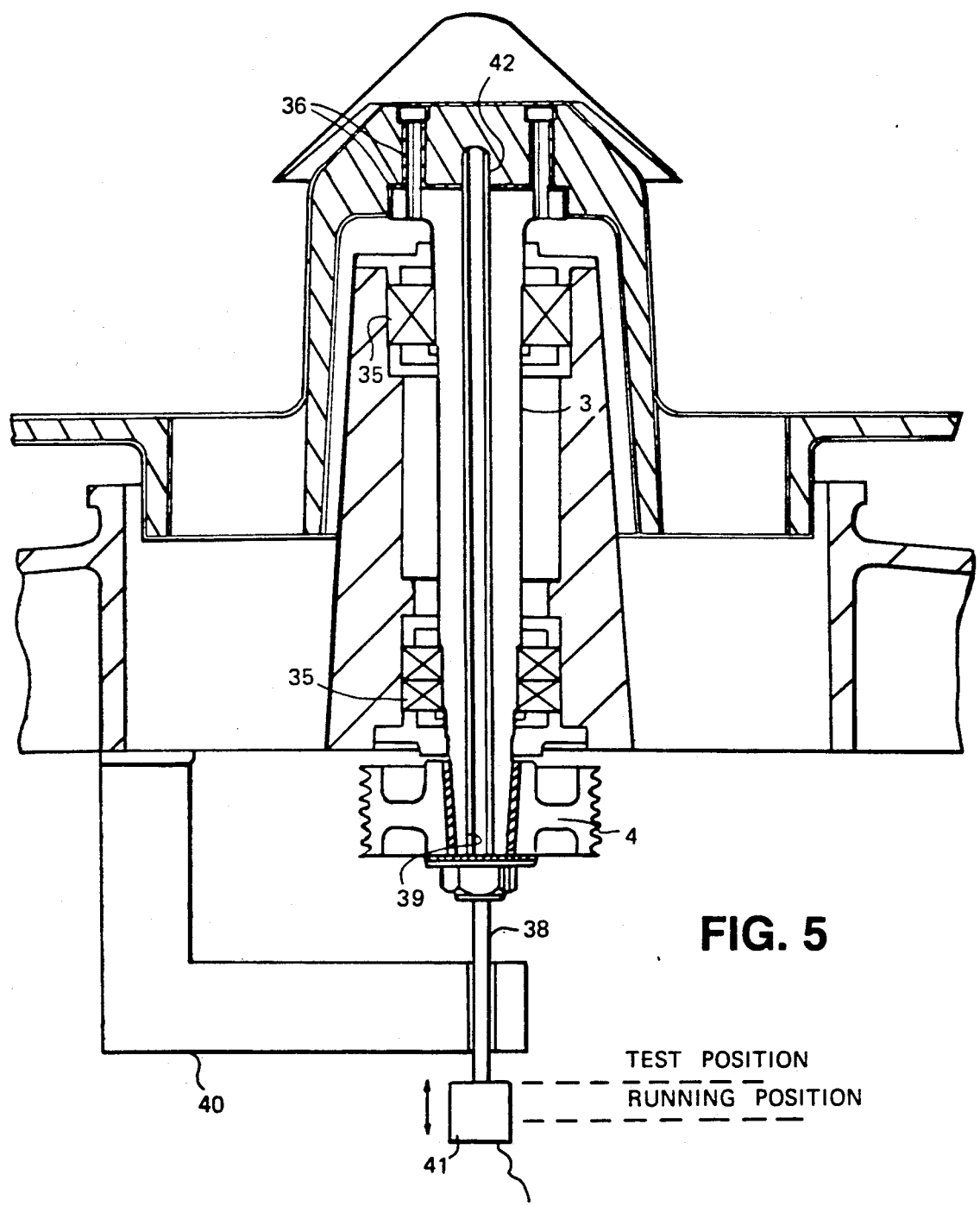
FIG. 5 is a cross-section through a spindle of a third embodiment of centrifuge in accordance with the present invention.

When the centrifuge is installed in conditions where condensation can occur in the area of the pulley 4 and the exposed parts of spindle 3, the arrangement illustrated in FIG. 5 is preferred. The basket 1 is insulated from the spindle 3 by means of hard insulating material (such as plasma sprayed aluminium oxide) 36 applied to the basket and/or spindle locating and mating surfaces. The spindle rotates in conventional uninsulated bearings 35 located in bearing housing 5 and a clearance hole 39 drilled through the spindle axis coincides with a blind clearance hole 42 drilled in the basket centre. An insulated metal rod 38 supported in sleeved bracket 40 passes through hole 39 into blind hole 42 and when raised by mechanism 41 makes electrical contact with the basket. A voltage applied between rod 38 and a stationary part of the centrifuge in contact with conducting liquid in the basket (i.e. feed indicator or wash jet) then tests the inert coating.

Figure 6:
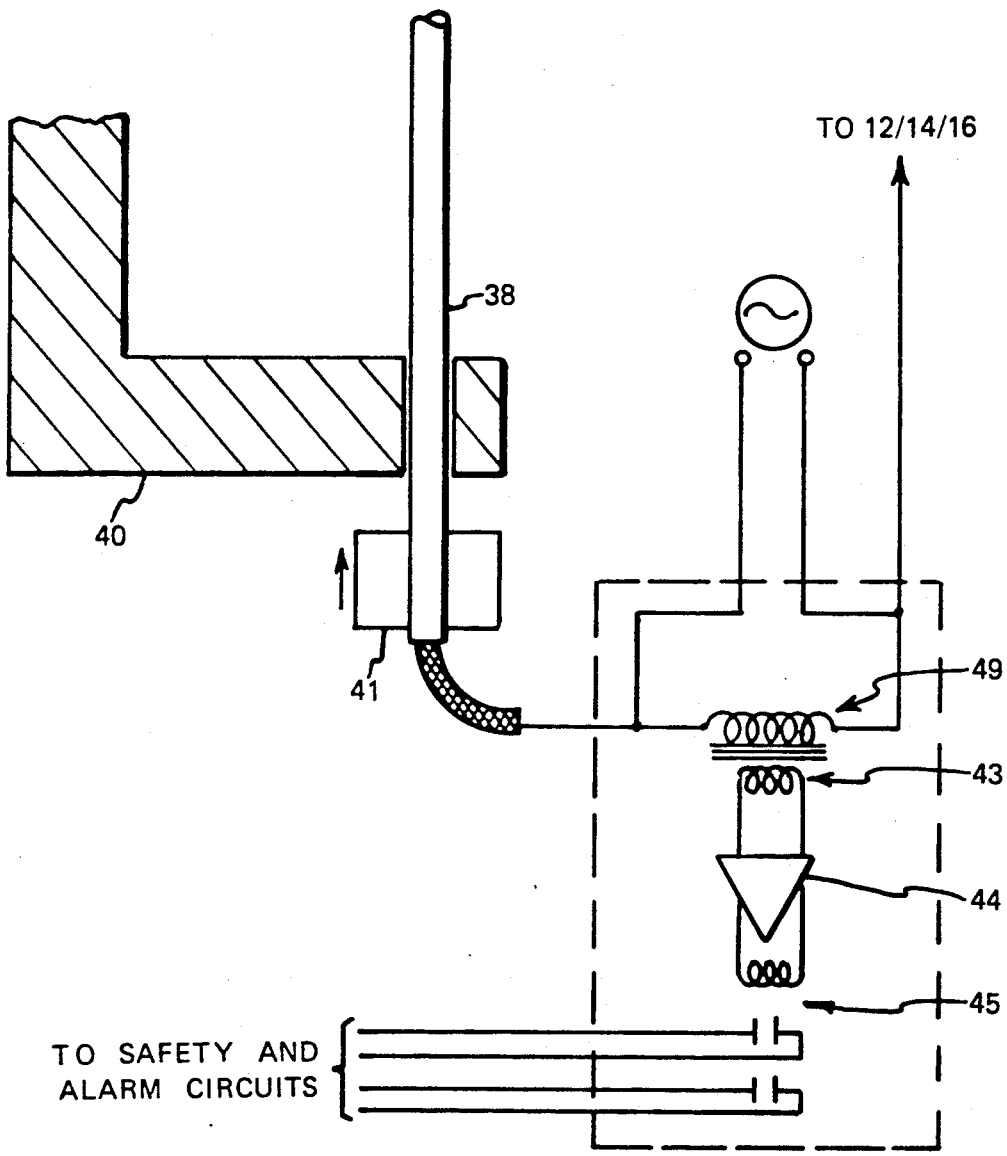
FIG. 6 is an electrical arrangement for the embodiments of FIGS. 4 and 5.

In a preferred electrical arrangement for a centrifuge constructed as FIGS. 4 or 5, illustrated in FIG. 6, the monitoring system contains an inductance 49 connected in parallel with the electrical connections to the insulated basket 1 and the uninsulated feed indicator or wash jet, the parallel connections being fed with an AC supply. The inert covering of the basket, if in good condition, can be considered the dielectric of a capacitor formed by the metal of the basket on one side of the inert coating and the conducting liquid on the other side. The inductance 42 is of such a value that at the frequency of the supply to the circuit it is in resonance with the capacitor and a relatively high resonance current flow in the circuit. This current is detected whilst allowing the resonance to continue by means of a second winding 43 on the inductance and a high impedance amplifier 44, or by other known means to close a relay 45 or the equivalent and to signal to the safety and interlocking circuits that the inert coating is in good condition. However, if the inert coating has failed and the conducting liquid is in contact with the metal of the basket the capacitor dielectric is shorted out, resonance does not occur, the relay 45 fails to close and signals inert coating failure—the system being "fail safe".

In an alternative electrical arrangement, the AC voltage may be applied to a capacitor bridge circuit, one leg of the bridge being the capacitance formed by the inert coating dielectric between the liquid contacting it on one side and the metal of the basket on the other. The bridge then remains in balance when the inert coating is in good condition, and goes off balance so that current now flowing in the balance arm of the bridge signals a faulty inert coating.

In all electrical arrangements known means may be used to compare the electrical current flow through a failed inert coating with a preset value and provide a warning signal when the current flow differs from the preset value. The arrangement may be extended to register the electrical current and compare this with a subsequent value to give a measure of the rate of deterioration of the inert covering and the appropriate safety and interlocking signals.

In applications in which the liquid conductivity changes to such an extent that it materially alters the current flowing through a failed inert coating a measure of the conductivity of the liquid is made by known means and using two liquid contacting devices, the resulting conductivity measure being used to alter the preset values to compensate for the changes in liquid conductivity. To this may be added known electronic equipment to record, display and, if required, print out the current values, ratios of current values, conductivity changes and so on, to give a measure of deterioration and rate of deterioration of the inert covering and the appropriate safety and interlocking signals.

I claim:

1. A method for testing, in situ, for imperfections in an inert coating of a rotatably mounted metal component fitted to and forming part of an apparatus, comprising the steps of:
   covering said coating with an electrically conductive liquid;
   applying an electrical voltage across said inert coating while said apparatus is operational and said component is rotating;
   monitoring the resulting current or applied voltage; and
   utilising said monitored current or voltage to provide an indication of the condition of said inert coating.

2. A method as claimed in claim 1, wherein said electrical voltage is applied to said liquid which is in contact with said inert coating.

3. A method as claimed in claim 2, wherein said liquid forms a layer over said inert coating, and a conductive member to which said voltage is applied contacts said liquid layer.

4. A method as claimed in claim 3, wherein said conductive member comprises a feed indicator slipper or shoe of a centrifuge.

5. A method as claimed in claim 2, comprising a jet or stream of conductive liquid directed onto said inert coating and to which said electrical voltage is applied.

6. A method as claimed in claim 5, wherein said jet or spray is from a washpipe, said electrical voltage being applied to said washpipe.

7. A method as claimed in claim 1, wherein said electrical voltage is applied directly to said inert coating.

8. A method as claimed in claim 1, wherein said rotatably mounted metal component of said apparatus comprises a metal basket.

9. A method as claimed in claim 1, wherein said rotatably mounted metal component is connected to a source of voltage.

10. A method as claimed in claim 9, wherein said electrical voltage is induced in said rotating metal component by means of a coil located thereon.

11. A method as claimed in claim 10, wherein an alternating voltage is applied.

12. A method as claimed in claim 11, wherein said alternating voltage is rectified to provide cathodic protection.

13. A method for testing, in situ, for imperfections in an inert coating of a metal basket of a centrifuge, using the method as claimed in claim 1 and wherein said metal basket comprises said rotatably mounted metal component.

14. An apparatus comprising a rotatably mounted metal component having an inert coating and forming part of said apparatus;
   means for covering said coating with an electrically conductive liquid when said component is rotating;
   a first electrical contact on or in use contacting said inert coating of said rotatably mounted component;
   a second electrical contact on or in use contacting said rotatably mounted metal component;
   said electrical contacts being linked by conductive parts of said apparatus to form a complete circuit via said conductive liquid if said inert coating on said rotating component is damaged; and
   means for detecting a completion of such a circuit.

15. An apparatus as claimed in claim 14, comprising means for applying an electrical voltage to said liquid which is in contact with said inert coating.

16. An apparatus as claimed in claim 15, comprising a conductive member, to which said voltage is applied, adapted to contact a layer of liquid over said inert coating.

17. An apparatus as claimed in claim 16, wherein said conductive member adapted to contact said liquid layer comprises a feed indicator slipper or shoe of a centrifuge.

18. An apparatus as claimed in claim 14, comprising means for directing a jet or stream of conductive liquid onto said inert coating, and means for applying an electrical voltage to said jet or stream.

19. An apparatus as claimed in claim 18, wherein said jet or spray is from a washpipe of a centrifuge, and said electrical voltage is applied to said washpipe.

20. Apparatus as claimed in claim 14, comprising an electrical connection directly on said inert coating.

21. Apparatus as claimed in claim 20, wherein said rotatably mounted component is mounted on a spindle, and a conductor passes in an insulated manner from a source of electrical voltage on said spindle to said inert coating.

22. Apparatus as claimed in claim 21, comprising an insulated conductor passing through an aperture in said spindle.

23. Apparatus as claimed in claim 20, wherein said rotatably mounted metal component of the apparatus comprises a metal basket of a centrifuge.

24. Apparatus as claimed in claim 14, comprising a coil connected to said rotatably mounted metal component, by means of which a voltage is induced.

25. Apparatus as claimed in claim 24, wherein an alternating voltage is induced.

26. Apparatus as claimed in claim 25, comprising rectifying means for applying a current of a single polarity in order to provide cathodic protection.

27. Apparatus as claimed in claim 14, comprising an electrical connector which is movable into and out of electrical contact with said rotatably mounted metal component.

28. Apparatus as claimed in claim 27, wherein said rotatably mounted metal component is mounted on a spindle, said spindle being insulated from the stationary components of the apparatus, and said movable electrical connector being movable into and out of contact with said spindle.

29. Apparatus as claimed in claim 28, comprising an electrical conductive rod which is movable into and out of contact with the base of an elongate recess provided in said spindle.

30. Apparatus as claimed in claim 27, wherein said rotatably mounted metal component is insulatedly mounted on a spindle, the electrical contact comprising a rod which is movable into and out of engagement with said rotatably mounted metal component through an aperture extending through said spindle.

31. Apparatus as claimed in claim 14, wherein said means for detecting completion of the circuit comprises an inductance connected in parallel with said electrical connections to said inert coating and comprising means for detecting resonance in the circuit.

32. Apparatus as claimed in claim 14, wherein said rotatably mounted metal component comprises a rotatably-mounted metal basket of a centrifuge.

33. A method for testing, in situ, for imperfections in an inert coating of a rotatable metal basket of a centrifuge, comprising the steps of:
covering said coating with liquid to be centrifuged;
applying an electrical voltage across said inert coating while said liquid is being centrifuged;
monitoring the resultant current or applied voltage; and
utilising said monitored current or voltage to provide an indication of the condition of said inert coating.

34. A method as claimed in claim 33, wherein said electrical voltage is applied to said liquid in contact with said inert coating.

35. A method as claimed in claim 33, wherein the electrical voltage is applied directly to the inert coating.

36. A centrifuge adapted to have an inert coating of a rotatably mounted metal basket tested for imperfections during operation comprising;
a first electrical contact on or in use contacting said inert coating of said basket;
a second electrical contact on or in use contacting said basket;
said electrical contacts being linked by conductive parts of the centrifuge to form a complete circuit via liquid being centrifuged if said inert coating is damaged; and
means for detecting completion of such a circuit.

37. A centrifuge as claimed in claim 36, comprising means for applying an electrical voltage to said liquid being centrifuged.

38. A centrifuge as claimed in claim 36, wherein said first electrical contact is directly on said coating.

* * * * *